United States Patent [19]

Pietsch et al.

[11] Patent Number: 4,748,268

[45] Date of Patent: May 31, 1988

[54] CONTINUOUS PROCESS FOR PRODUCTION OF METHACRYLIC ACID ESTER OF $C_1$ TO $C_4$ ALIPHATIC ALCOHOL

[75] Inventors: Stephen J. Pietsch, Oak Park; Houssam M. Naim, Naperville, both of Ill.

[73] Assignee: Amoco Corporation, Chicago, Ill.

[21] Appl. No.: 891,760

[22] Filed: Jul. 31, 1986

[51] Int. Cl.$^4$ ............................................. C07C 67/08
[52] U.S. Cl. ................................................... 560/205
[58] Field of Search ......................................... 560/205

[56] References Cited

U.S. PATENT DOCUMENTS

| | | | |
|---|---|---|---|
| 3,821,286 | 6/1974 | Pai et al. | 560/205 |
| 4,329,492 | 5/1982 | Andoh et al. | 560/205 |
| 4,435,594 | 3/1984 | Matsumura et al. | 560/205 |
| 4,474,981 | 10/1984 | Katoh et al. | 560/205 |

OTHER PUBLICATIONS

Levenspiel, Octave Chemical Reaction Engineering, 2nd Ed. (1972) John Wiley & Sons, Publ. pp. 97, 98, 144 and 145.

*Primary Examiner*—Michael L. Shippen
*Attorney, Agent, or Firm*—Reed F. Riley; William H. Magidson; Ralph C. Medhurst

[57] ABSTRACT

A continuous process for the production of methacrylic acid ester of a $C_1$ to $C_4$ saturated aliphatic alcohol in the presence of a catalyst is disclosed. This process contemplates continuously introducing into a plug-flow reactor a feed stream containing methacrylic acid, a $C_1$ to $C_4$ saturated aliphatic alcohol in stoichiometric exesss relative to the methacrylic acid present, an esterification catalyst, and a liquid organic substance having a volatility no greater than that of methacrylic acid. The feed stream thus introduced into the plug-flow reactor is preferably maintained at substantially atmospheric pressure, while the contained methacrylic acid reactant is held at an esterification temperature and for a time period sufficient to esterify at least a portion of the introduced methacrylic acid. The admixture thus produced is continuously fractionated, preferably in a distillation zone or column, into a vaporized distillate stream and a liquid bottoms stream. The distillate stream has a relatively greater methacrylic acid ester content than the bottoms stream. A portion of the bottoms stream, constituted primarily by the liquid organic substance and the esterification catalyst, is recycled to the reactor while the remainder is purged.

8 Claims, 1 Drawing Sheet

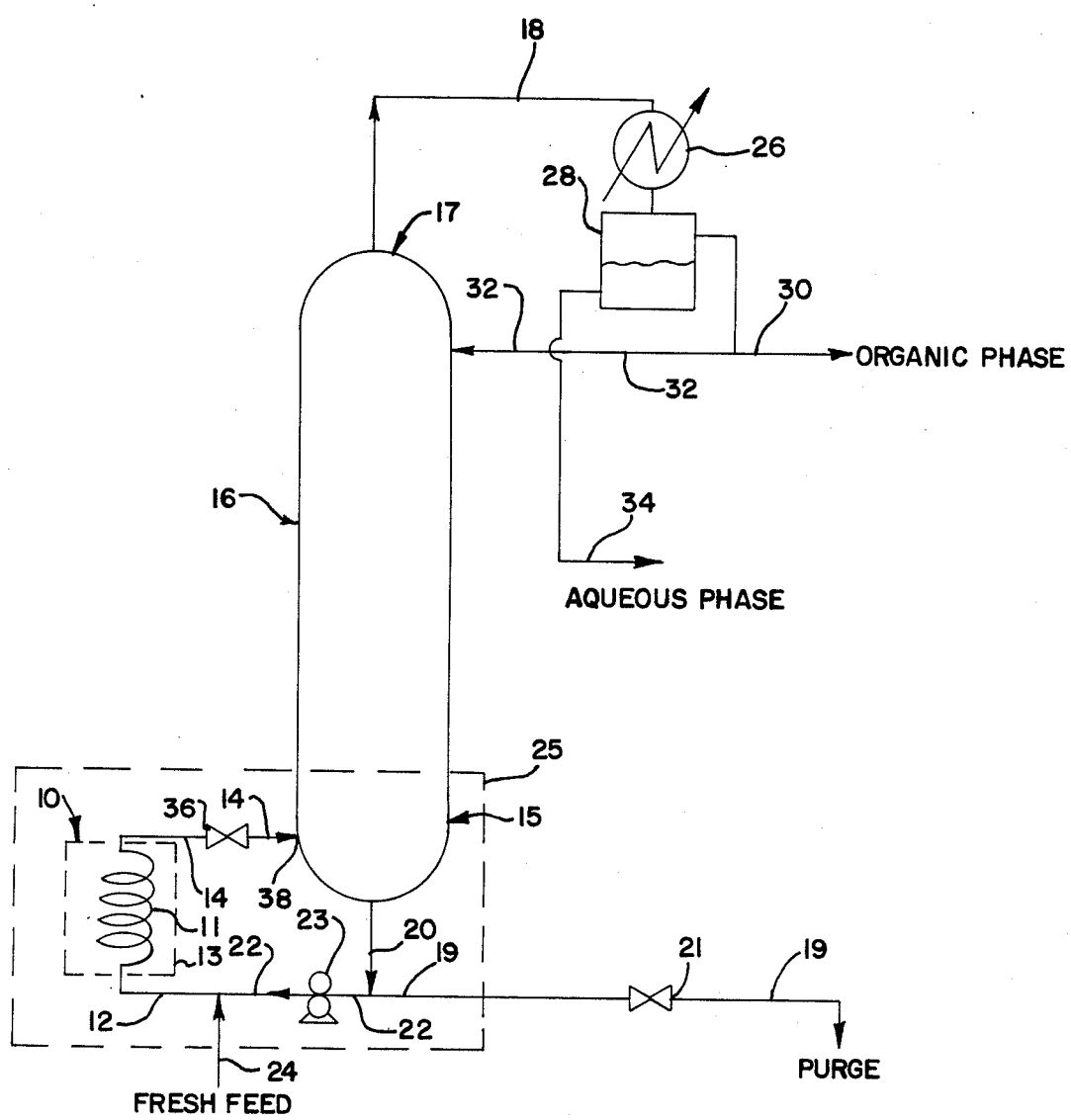

CONTINUOUS PROCESS FOR PRODUCTION OF METHACRYLIC ACID ESTER OF $C_1$ TO $C_4$ ALIPHATIC ALCOHOL

TECHNICAL FIELD OF THE INVENTION

The present invention relates to esterification of methacrylic acid. More particularly, the present invention is directed to a process that provides continuous esterification of methacrylic acid in a process stream that includes appreciable amounts of relatively high boiling impurities as well.

BACKGROUND OF THE INVENTION

Methacrylic acid esters of saturated aliphatic alcohols, e.g. methyl methacrylate (MMA), are useful precursors of acrylic or acrylic-type polymers. Such polymers, in turn, exhibit good transparency, weatherability and physical strength properties, and thus are eminently well suited for a wide variety of applications. Typical end uses for MMA-derived polymers include acrylic sheet that can be fabricated into signs, advertising displays, lighting fixtures, glazing materials, structural panels and the like, molding resins for automobile tail-light lenses, plumbing fixtures and the like, as well as constituents of a variety of surface coatings, adhesives, inks, floor polishes and the like.

The esterification of methacrylic acid with a saturated aliphatic alcohol such as methanol is, of course, well known in the art. One such esterification process is described in U.S. Pat. No. 3,639,460 to Wenzel et al. In that particular process the esterification reaction is carried out in what is substantially a continuous flow stirred tank reactor (CSTR) and in the presence of an excess of methacrylic acid (MA) in the reactor.

In such conventional MA-esterification processes, liquid organic by-products, typically present in appreciable concentration inasmuch as most commercial CSTRs exhibit relatively low conversion rates and provide no practical type of a purge stream, are generally undesirable. Current MA-esterification technology thus typically requires separation of such by-products from the MA, or minimization of the concentration of the by-products relative to the MA present, before the MA is esterified.

However, conventional methods for separating these liquid organic by-product substances from the crude, synthesized methacrylic acid prior to esterification are economically unattractive, principally because of unacceptable product losses. Moreover, energy costs are often significant.

The process of the present invention allows for low-cost, continuous-flow, catalytically induced, relatively high-conversion esterification of a crude methacrylic acid feed stream. The methacrylic acid-containing feed stream can contain not only the unreacted alcohol and methacrylic acid, but also appreciable amounts of by-product impurities as well. One further advantage of the present invention is that high-boiling impurities that are present can be advantageously utilized as part of the esterification medium. That is, the impurities need not be separated from the crude methacrylic acid prior to the esterification step but can be used advantageously to dilute the reactants with attendant better process control.

SUMMARY OF THE INVENTION

The methacrylic acid esterification process contemplated by the present invention utilizes an excess of the esterifying alcohol and a plug-flow type of reactor. A feed stream containing methacrylic acid, a $C_1$ to $C_4$ aliphatic alcohol in stoichiometric excess relative to the methacrylic acid present, an esterification catalyst, and a liquid organic substance having a volatility no greater than that of methacrylic acid are fed to the reactor. This feed stream is maintained in the reactor at substantially atmospheric pressure, at an esterification temperature, and for a time period sufficient to esterify at least a portion of the introduced methacrylic acid. An admixture produced within the reactor contains the methacrylic acid ester, unreacted methacrylic acid, unreacted $C_1$ to $C_4$ aliphatic alcohol, the esterification catalyst, water, and sundry other reaction products.

The produced admixture is continuously fractionated, preferably within a distillation zone or column, into a distillate stream and a bottoms stream. The distillate stream has a relatively greater methacrylic acid ester content than the bottoms stream. The bottoms stream, on the other hand, contains relatively non-volatile liquid organic substances, some methacrylic acid ester, some methacrylic acid, some alcohol, the catalyst, and water. A portion of the bottoms stream is recycled to the reactor, and the remainder is purged.

BRIEF DESCRIPTION OF THE DRAWING

In the drawing, the FIGURE is a process flow diagram illustrating a system embodying the principles of the continuous-flow methacrylic acid esterification process of the present invention.

DETAILED DESCRIPTION OF PREFERRED EMBODIMENT

While the present invention is susceptible to embodiment in various forms, there is shown in the accompanying FIGURE, and hereinafter described in detail, a preferred embodiment of the invention. The present disclosure is to be considered as an exemplification of the invention without limitation to the specific embodiment illustrated, however.

Referring to the accompanying FIGURE, a reactor feed stream is introduced into a plug-flow reactor 10 via a reactor-supply or reactor-feed pipe 12. Inasmuch as the desired esterification reaction is reversible, a plug-flow type of reactor would normally not be selected. It has been found in the present process, however, that the utilization of a plug-flow type of reactor affords certain advantages that will be described hereinbelow in greater detail.

The reactor feed stream contains crude methacrylic acid and a $C_1$ to $C_4$ aliphatic alcohol as reactants, an esterification catalyst such as sulfuric acid, and at least one liquid organic substance having a volatility no greater than that of methacrylic acid. Generally, the reactor feed stream contains a variety of liquid organic substances, such as those that are by-products of an upstream methacrylic acid production process.

Illustrative of suitable $C_1$ to $C_4$ saturated aliphatic alcohols that can be used for esterification purposes in accordance with the principles of the present invention are methanol, ethanol, n-propanol and n-butanol. Methanol is preferred.

Suitable esterification catalysts are well known. Sulfuric acid is illustrative and is preferred.

The feed stream to reactor 10 is maintained at substantially atmospheric pressure, and is maintained at an esterification temperature for a time period sufficient to esterify at least a portion of the methacrylic acid introduced into reactor 10. Typical esterification temperatures are in the range of about 100° C. (about 212° F.) to about 160° C. (about 320° F.).

The reactor effluent is constituted by an admixture that contains the methacrylic acid and the aliphatic alcohol reactants, the desired ester, as well as any by-products that may have been formed during esterification or that may have been introduced as part of the feed stream.

Reactor 10 can include a spiral, or coiled, tubular reaction zone 11 surrounded by a heat exchanger 13 for supplying heat to the reaction zone 11, as shown in the FIGURE. Alternatively, the plug-flow reactor can have any appropriate heat-exchanger configuration, so long as plugflow can be maintained through the reactor.

The reactor effluent is conveyed away from reactor 10, via a conduit 14, to a suitable fractionation zone, such as into a sump portion 15 of a distillation column 16. The reactor effluent is continuously fractionated, preferably at a subatmospheric pressure, within distillation column 16, into a relatively volatile distillate or overhead stream and a relatively nonvolatile bottoms stream. The vaporized distillate stream rises through distillation column 16 and exits from the upper or head portion 17 thereof via an overhead vapor pipeline 18. The liquid bottoms stream exits from the sump portion 15 of distillation column 16 via a bottom discharge pipeline 20.

The distillate, i.e. the overhead vapor stream, from distillation column 16 has a relatively greater methacrylic acid ester content than the bottoms stream and is condensed in an overhead condenser 26. The resulting condensate is fed to a suitable separator 28, such as the decanter shown in the accompanying FIGURE, for further liquid-liquid separation as will be discussed in greater detail below.

A portion of the bottoms stream is returned, as recycle, to the plug-flow reactor 10. The remainder of the bottoms stream can be readily purged from the system, in a continuous or semicontinuous manner, via a purge line 19 as shown. The purge line 19 can include a valve 21, which can be remotely operated.

A bottoms return conduit 22 supplies the returned bottoms stream portion to plug-flow reactor 10 via reactor feed pipe 12, as is shown. To assist the return of the recycled bottoms stream to reactor 10, and to maintain a desired reaction pressure within the pipeline reactor 10, conduit 22 preferably includes a suitable pump 23, such as a rotary, positive-displacement pump or the like.

The feed stream to plug-flow reactor 10 is constituted by the returned bottoms stream portion, recycled via conduit 22, and a fresh feed stream that is fed to reactor 10 via a fresh-feed pipeline 24. The fresh feed may include crude methacrylic acid, the $C_1$ to $C_4$ aliphatic alcohol that is to be esterified therewith, and the esterification catalyst, as well as upstream methacrylic acid synthesis by-products and other impurities. Preferably, bottoms return conduit 22 and fresh-feed pipeline 24 are combined before entry into the reactor so as to continuously feed to reactor 10 via reactor supply pipe 12 a substantially uniform reaction admixture over a preselected period of time. The $C_1$ to $C_4$ alcohol is present in the reactor feed stream in stoichiometric excess relative to the methacrylic acid present.

Specifically, when the contemplated alcohol is methanol, such methanol is present in the plug-flow reactor feed stream in an excess of up to about 70 mole percent, based on the amount of methacrylic acid that is present in reactor supply pipe 12.

The bottoms stream discharged from distillation column 16 via bottoms discharge pipeline 20 contains a major portion of the liquid organic substance, and the esterification catalyst, initially supplied to the system via fresh-feed pipeline 24. Preferably, the bottoms stream contains substantially all, and the overhead vapor stream contains substantially none, of the aforementioned liquid organic substance or substances and the esterification catalyst supplied to the system via fresh-feed pipeline 24.

In operation, the volumetric ratio of the returned bottoms stream portion to the fresh feed in the total feed supplied to plug-flow reactor 10 can be in the range of about 5 to about 200. Preferably, this volumetric ratio is about 5 to about 20.

When the desired methacrylic acid ester is methyl methacrylate, the volumetric ratio of the recycled distillation column bottoms stream to the reactor feed stream is preferably about 0.8 to about 0.995, and more preferably is about 0.8 to about 0.95.

A recirculation loop 25 for the distillation column 16 comprises the bottom or sump portion 15 of distillation column 16, the plug-flow reactor 10, and the various conduits 12, 14, 20 and 22, as shown in the FIGURE. Preferably, the heat exchanger 13 in addition to providing heat to the reaction zone 11, as mentioned above, also provides the necessary heat input for the distillation column 16. Thus, another advantage of the present invention is that the produced methacrylic acid ester can be continuously recovered from the distillation column overhead in a relatively pure form and at a relatively high yield while an accumulation of undesirable by-products in the system is avoided.

The produced methacrylic acid ester is readily recovered in distillation column 16 employing well-known azeotropic distillation methods. The overhead vapor that passes out of distillation column 16 via overhead pipeline 18 is passed through the overhead condenser 26 and is thus liquefied. The resultant condensate, which typically comprises an aqueous phase and an organic phase, is then passed to separator 28 for separation of these two phases. A preferred separator is a decanter. The aqueous phase is withdrawn from separator 28 via a conduit 34. A portion of the organic phase is passed from separator 28 via a conduit 30 to storage or further processing, as desired. The remainder of the organic phase is returned from separator 28 to distillation column 16, as reflux, via a liquid reflux pipeline 32.

The liquid organic substance that is recirculated in the recirculation loop 25, also sometimes referred to herein as a relatively high-boiling impurity or as "heavies", is primarily a by-product of an upstream methacrylic acid synthesis step, which by-product need not be separated from the crude methacrylic acid feed stream before this acid is esterified. This liquid organic substance usually is constituted by 2,5-dimethylcyclopentenone, 3,5,5-trimethylbutyrolactone, and heavier substances, in various relative amounts. Typically, a mixture of these reaction by-products is present in varying amounts in plug-flow reactor supply pipe 12, feeding plug-flow reactor 10. The liquid organic substance serves as a diluent for the reactants. For instance, the concentration of the alcohol in the reaction admixture is reduced, thereby permitting the use of excess alcohol without the formation of undesirable ethers. Inasmuch as methacrylic acid concentration is also diluted, the undesired conversion of methacrylic acid to acetone and CO is also minimized.

Refluxing the methacrylic acid ester to distillation column 16 via liquid reflux pipeline 32 allows for relatively easy removal of the water of reaction. Also, because the catalyst present in distillation column feedpipe 14 remains in the distillation column bottoms stream, unreacted methacrylic acid and the catalyst, along with the above-mentioned by-products having relative volatilities less than or equal to that of methacrylic acid, can readily be purged from the system via purge line 19 to the extent desired.

When the methacrylic acid ester to be produced is methyl methacrylate, the mole ratio of the $C_1$ to $C_4$ aliphatic alcohol-to-methacrylic acid reactants present in the feed stream to plug-flow reactor 10 is preferably about 1.1 to about 1.7. More preferably, the mole ratio of the alcohol-to-methacrylic acid in the plug-flow reactor feed stream is about 1.2 to about 1.5.

When the esterification catalyst is sulfuric acid, the sulfuric acid concentration in the distillation column feed stream may be about 5 to about 50 wt. %, and preferably is about 15 to about 30 wt. %, based on the weight of the distillation column feed stream.

When methyl methacrylate is produced in a continuous or so-called "steady-state" operation, the organic phase portion that is returned to distillation column 16 as reflux is primarily methyl methacrylate with relatively minor amounts of methanol and water also present. The aqueous phase is mostly water, but can include minor amounts of methanol and methyl methacrylate. The fresh feed to plug-flow reactor 10 comprises methanol, crude methacrylic acid, the relatively heavy by-products, and the esterification catalyst. The process purge stream, of mostly by-product and catalyst, can include relatively minor amounts of unreacted methacrylic acid and methanol, as well as some methyl methacrylate and water. That portion of the bottoms stream that is returned to plug-flow reactor 10 via bottoms return conduit 22 usually includes less than about 10 wt. % of the methyl methacrylate esterification reactants and products, with the remainder thereof being the relatively heavy by-products, and the esterification catalyst.

During steady-state operation about 0.1 to about 2 wt. % of the bottoms stream in bottoms discharge conduit 20 is purged from recirculation loop 25 via purge line 19 to modulate the amount of bottoms from distillation column 16 that is returned as recycle to plug-flow reactor 10 via conduit 22. Preferably, the relatively heavy by-product concentration in plug-flow reactor 10 is maintained at about 55 to about 75 percent by weight.

To produce methyl methacrylate, the esterification temperature of the feed stream introduced into plug-flow reactor 10 is preferably about 100° C. (about 212° F.) to about 135° C. (about 275° F.) and the reactor residence time, i.e. that time period during which the introduced feed stream is held within plug-flow reactor 10, is preferably about 5 seconds to about 5 minutes. More preferably, the esterification temperature is about 120° C. (about 248° F.) to about 135° C. (about 275° F.), and the reactor residence time is about 30 seconds to about 2 minutes.

The pressure within distillation column 16 is preferably subatmospheric, more preferably about 250 millimeters of mercury. The pressure within the plug-flow reactor 10 is preferably maintained at least about 10 pounds per square inch in excess of the internal pressure of distillation column 16.

Pressure within the tubular reaction zone 11 can be maintained by a suitable back-pressure or throttle valve 36, which can be incorporated into conduit 22 as is shown in the accompanying FIGURE. Valve 36 can be remotely operated. Preferably, valve 36 is spaced relatively close to a distillation column feed inlet 38, so that the distillation column feed stream flashes into the bottom or sump portion 15 of distillation column 16 after being reduced in pressure.

The present invention is further illustrated by the following process example:

EXAMPLE

Continuous Production of Methyl Methacrylate in a Plug-Flow Reactor and in the Presence of Excess Methanol The esterification system shown in the FIGURE was operated under the following conditions.
Reactor Temperature: 135° C. (275° F.)
Reactor Back Pressure: 10 psi
Reactor Residence Time: 5 seconds
Distillation Column Bottoms Temperature: 129.4° C. (about 265° F.)
$H_2SO_4$ concentration: 35.6 wt. %
MeOH/MA in Fresh Feed: 1.31 (mole/mole)
Bottoms Recirculation Rate/Fresh Feed Rate: about 195 (volume/volume).

The observed material balance is set forth in Table I below.

TABLE I

| COMPONENT, grams/hr. | MMA PRODUCTION RATE | | | |
| --- | --- | --- | --- | --- |
| | FEED TO DISTILLATION COLUMN | PURGE FROM SYSTEM | OVERHEAD | |
| | | | ORGANIC PHASE[2] | AQUEOUS PHASE[2] |
| MA | 340.7 | 5.7 | — | — |
| MMA | — | 3.3 | 392.2 | 2.0 |
| MeOH | 166.4 | 2.0 | 12.4 | 16.3 |
| $H_2SO_4$ | 38.5 | 38.5 | — | — |
| $H_2O$ | — | 1.5 | 9.1 | 64.2 |
| Heavies[1] | 57.0 | 57.0 | — | — |
| Totals: | 602.6 | 108.0 | 413.7 | 82.5 |

[1]liquid organic substances having a volatility no greater than that of MA
[2]organic phase that is withdrawn from system
[3]aqueous phase that is withdrawn from system What has been illustrated and described herein is a process for the continuous esterification of methacrylic acid with a $C_1$ to $C_4$ saturated aliphatic alcohol. While the process of the present invention has been illustrated and described with reference to a preferred embodiment, the present invention is not to be limited thereto. On the contrary, alternatives, changes or modifications will become apparent to those skilled in the art upon reference to the foregoing description and the ensuing claims. For example, while the process has been discussed in connection with the esterification of methacrylic acid to methyl methacrylate, the process can be used to produce acrylate esters and other methacrylate esters as well. Accordingly, such alternatives, changes and modifications are to be considered as forming a part of the invention insofar as they fall within the spirit and scope of the appended claims.

We claim:

1. A continuous process for production of methacrylic acid ester of a $C_1$ to $C_4$ saturated aliphatic alcohol in the presence of an esterification catalyst, which process comprises the steps of:

continuously introducing into a plug-flow reactor a feed stream containing methacrylic acid, a $C_1$ to $C_4$ saturated aliphatic alcohol in stoichiometric excess relative to the methacrylic acid present, a sulfuric acid esterification catalyst, and relatively high boiling liquid organic substances which include at least one member from the group consisting of 2,5-dimethylcyclopentenone and 3,5,5-trimethylbutyrolactone having a volatility no greater than that of methacrylic acid, such that said liquid organic substances constitute between about 55 and about 75 percent by weight of the contents of said reactor;

maintaining the introduced feed stream in the plug-flow reactor at substantially atmospheric pressure and at an esterification temperature for a time period sufficient to product a relatively high conversion esterification and to produce a reactant and reaction product admixture;

continuously fractionating the produced admixture at a subatmospheric pressure into a distillate stream having a relatively greater methacrylic acid ester content and a bottoms stream having a relatively lesser methacrylic acid ester content and containing said liquid organic substances and said sulfuric acid; and returning at least about 98 wt. % to about 99.9 wt. % of said bottoms stream to the plug-flow reactor.

2. The process in accordance with claim 1 wherein the alcohol is methanol, and wherein the mole ratio of the alcohol to the methacrylic acid in the feed stream is about 1.1 to about 1.7.

3. The process in accordance with claim 2 wherein the mole ratio of the alcohol to the methacrylic acid in the feed stream is about 1.2 to about 1.5.

4. The process in accordance with claim 1 wherein the esterification temperature is about 100° C. to about 160° C.

5. The process in accordance with claim 1 wherein the time period within the plug-flow reactor is about 5 seconds to about 5 minutes.

6. The process in accordance with claim 1 wherein the time period within the plug-flow reactor is about 30 seconds to about 2 minutes.

7. The process in accordance with claim 1 wherein the aliphatic alcohol is methanol, wherein the esterification temperature is about 120° C. to about 135° C., and wherein the time period within the plug-flow reactor is about 30 seconds to about 2 minutes.

8. The process in accordance with claim 1 wherein the subatmospheric pressure during fractionation is about 250 millimeters of mercury.

* * * * *